United States Patent
Aubrun et al.

(10) Patent No.: US 9,603,782 B2
(45) Date of Patent: Mar. 28, 2017

(54) ANHYDROUS SOFT SOLID COMPOSITION COMPRISING HYDROPHOBIC SILICA AEROGEL PARTICLES, AT LEAST ONE OIL AND AT LEAST ONE SOLID FATTY SUBSTANCE

(75) Inventors: Odile Aubrun, Antony (FR); Justyna Frelichowska, Rijswijk (NL)

(73) Assignee: L'Oreal, Paris (FR)

( * ) Notice: Subject to any disclaimer, the term of this patent is extended or adjusted under 35 U.S.C. 154(b) by 192 days.

(21) Appl. No.: 13/996,315

(22) PCT Filed: Dec. 7, 2011

(86) PCT No.: PCT/EP2011/072093
§ 371 (c)(1),
(2), (4) Date: Sep. 27, 2013

(87) PCT Pub. No.: WO2012/084522
PCT Pub. Date: Jun. 28, 2012

(65) Prior Publication Data
US 2014/0017289 A1    Jan. 16, 2014

Related U.S. Application Data

(60) Provisional application No. 61/431,215, filed on Jan. 10, 2011.

(30) Foreign Application Priority Data

Dec. 21, 2010   (FR) ...................................... 10 60891

(51) Int. Cl.
| | | |
|---|---|---|
| A61K 33/00 | (2006.01) |
| A61K 8/02 | (2006.01) |
| A61K 8/00 | (2006.01) |
| A61K 47/00 | (2006.01) |
| A61K 8/25 | (2006.01) |
| A61K 8/37 | (2006.01) |
| A61K 8/92 | (2006.01) |
| A61Q 15/00 | (2006.01) |

(52) U.S. Cl.
CPC .............. *A61K 8/0241* (2013.01); *A61K 8/25* (2013.01); *A61K 8/375* (2013.01); *A61K 8/92* (2013.01); *A61Q 15/00* (2013.01); *A61K 2800/412* (2013.01)

(58) Field of Classification Search
None
See application file for complete search history.

(56) References Cited

U.S. PATENT DOCUMENTS

2007/0244442 A1* 10/2007 Chowhan ...................... 604/191

OTHER PUBLICATIONS

Product Information Personal Care; Dow Corning VM-2270 Aerogel Fine Particles; 5 pages; dated Jul. 12, 2007; downloaded Mar. 5, 2015.*

* cited by examiner

*Primary Examiner* — Jeffrey T Palenik
(74) *Attorney, Agent, or Firm* — Polsinelli PC

(57) ABSTRACT

The present invention relates to an anhydrous composition comprising, in a cosmetically acceptable medium: a) at least hydrophobic silica aerogel particles with a specific surface area per unit of mass ($S_M$) ranging from 500 to 1500 m²/g, preferably from 600 to 1200 m²/g and better still from 600 to 800 m²/g, and a size expressed as the mean volume diameter (D[0.5]) ranging from 1 to 30 μm; b) at least one solid fatty substance; c) at least one oil; the said composition having a hardness measured at 32° C. and at a humidity of 40% ranging from 15 kPa to 150 kPa and preferably ranging from 20 kPa to 100 kPa. The present invention also relates to a cosmetic process for treating and/or caring for human keratin materials, characterized in that it consists in applying to the surface of the keratin material at least one composition as defined previously. The present invention also relates to a cosmetic process for treating human perspiration and/or perspiration-related body odor, which consists in applying to the surface of a human keratin material at least one composition as defined previously comprising at least one deodorant active agent and/or one antiperspirant active agent.

19 Claims, No Drawings

ANHYDROUS SOFT SOLID COMPOSITION COMPRISING HYDROPHOBIC SILICA AEROGEL PARTICLES, AT LEAST ONE OIL AND AT LEAST ONE SOLID FATTY SUBSTANCE

CROSS REFERENCE TO RELATED APPLICATIONS

This application is a National Phase filing under 35 U.S.C. §371 of PCT/EP2011/072093 filed on Dec. 7, 2011; and this application claims priority to Application No. 1060891 filed in France on Dec. 21, 2010, and claims the benefit of U.S. Provisional Application No. 61/431,215; the entire contents of all are hereby incorporated by reference.

In the field of deodorants and antiperspirants, "soft solid" compositions constitute a category of products that is appreciated by consumers for their efficacy and their cosmetic qualities (soft, dry feel). They are likened to solid compositions that soften under the effect of a stress such as spreading over the surface of the skin or, for example, by extrusion through a device with a perforated wall (grille).

"Soft solid" compositions, by virtue of their fondant texture, may also be increased in value as care products for human keratin materials such as the skin or the lips, or as massage products, balms or pomades, or lipcare sticks. These products contain in the majority volatile silicones that contribute towards the lightness and the non-greasy feel, but pose numerous drawbacks. These silicones make the industrial manufacturing processes cumbersome for safety reasons. They are not entirely satisfactory in environmental terms.

It has already been proposed to use silicas in antiperspirant and/or deodorant "soft solid" compositions.

U.S. Pat. No. 4,937,069 describes semi-solid antiperspirant compositions formed from 10-50% antiperspirant active agent, 2% to 6% thickener containing at least 2% silica relative to the total composition, 2-15% solid thickening emollient, 2-15% non-volatile liquid emollient and 30-70% volatile silicone.

U.S. Pat. No. 6,737,048 describes antiperspirant compositions in the form of water-in-oil emulsions stabilized with an alkyldimethicone copolyol, and thickened with structuring agents of acetylated sugar type (cellobiose). Optionally, they may comprise hydrophobic silicas in concentrations of less than 2%, with specific surface areas of less than 350 $m^2/g$.

Patent application US 2004/0001891 (Bayer) describes a perfume encapsulation system based on starch and hydrophobic silica, which may be incorporated into antiperspirants sticks (Example 4).

It has also been proposed to use silicas in lipstick wands for limiting exudation, in U.S. Pat. No. 5,843,407.

These formulations are not entirely satisfactory as regards the cosmetic properties obtained.

There is thus still a need to produce soft solid formulations, especially deodorant and/or antiperspirant products, which have a dry, non-greasy feel, without it being necessary to use a volatile silicone and without the drawbacks listed previously.

The Applicant has discovered that this objective can be achieved by using an anhydrous "soft solid" composition comprising, in a cosmetically acceptable medium:
 a) at least particular hydrophobic silica aerogel particles that will be defined later in greater detail;
 b) at least one solid fatty substance;
 c) at least one oil;
the said composition having a hardness measured at 32° C. and at a humidity of 40% ranging from 15 kPa to 150 kPa and preferably ranging from 20 kPa to 100 kPa.

The use of the silica aerogel particles also makes it possible to improve the remanence of the cosmetic properties afforded by the composition on keratin materials, in particular the skin (in particular the dry feel, the non-greasy feel and the deodorant activity), especially by limiting the impact of the perspiration on the skin.

This discovery forms the basis of the invention.

The present invention thus relates to an anhydrous composition comprising, in a cosmetically acceptable medium:
a) at least hydrophobic silica aerogel particles with a specific surface area per unit of mass (SM) ranging from 500 to 1500 $m^2/g$, preferably from 600 to 1200 $m^2/g$ and better still from 600 to 800 $m^2/g$, and a size expressed as the mean volume diameter (D[0.5]) ranging from 1 to 1500 µm;
b) at least one solid fatty substance;
c) at least one oil; the said composition having a hardness measured at 32° C. and at a humidity of 40% ranging from 15 kPa to 150 kPa and preferably ranging from 20 kPa to 100 kPa.

The present invention also relates to a cosmetic process for treating and/or caring for human keratin materials, characterized in that it consists in applying to the surface of the keratin material at least one composition as defined previously.

The present invention also relates to a cosmetic process for treating human perspiration and/or perspiration-related body odour, which consists in applying to the surface of a human keratin material at least one composition as defined previously comprising at least one deodorant active agent and/or one antiperspirant active agent.

Other subjects of the invention will emerge later in the description.

The term "anhydrous composition" means a composition containing less than 2% by weight of water, or even less than 0.5% water, and especially free of water, the water not being added during the preparation of the composition but corresponding to the residual water provided by the mixed ingredients.

The term "cosmetically acceptable" means compatible with the skin and/or its integuments or mucous membranes, having a pleasant colour, odour and feel and not causing any unacceptable discomfort (stinging, tautness or redness) liable to discourage the consumer from using this composition.

The term "solid fatty substance" means a lipophilic compound that is solid at room temperature (20-25° C.).

The term "human keratin materials" means the skin (of the body, face and around the eyes), hair, eyelashes, eyebrows, bodily hair, nails, lips or mucous membranes.

The term "antiperspirant" means any substance which has the effect of reducing the flow of sweat and/or of reducing the sensation of moisture associated with human sweat, and/or of masking human sweat.

The term "deodorant active agent" refers to any substance that is capable of masking, absorbing, improving and/or reducing the unpleasant odour resulting from the decomposition of human sweat by bacteria.

Hardness

The compositions according to the invention that are termed "soft solids" have a hardness measured at 32° C. and at a humidity of 40% ranging from 15 kPa to 150 kPa and preferably ranging from 20 kPa to 100 kPa.

The hardness is defined as the maximum stress force $F_{max}$ measured by texturometry during the penetration of a cylindrical probe into the sample of formulation, assessed under precise measuring conditions as follows.

The formulae are poured hot into jars 9 cm in diameter and 3 cm deep (i.e.: "Favorit Soft" jars from RPC Bramlage GmbH). Cooling is performed at room temperature. The hardness of the formulae is measured after an interval of 24 hours. The jars containing the samples are characterized by texturometry using a texturometer such as the TA-XT2 machine sold by the company Rheo, according to the following protocol:

At a temperature of 32° C. and at a relative humidity of 40%, a cylindrical stainless-steel probe with a spindle 2 mm in diameter is brought into contact with the sample at a speed of 1 mm/sec. The measuring system detects the interface with the sample, with a detection threshold equal to 0.005 newtons. The probe penetrates 0.3 mm into the sample, at a speed of 0.1 mm/s. The measuring machine records the change in force measured in compression over time, during the penetration phase. The hardness of the sample corresponds to the average of the maximum force values detected during penetration, over at least three measurements. After measurement, the relaxation time is 1 second, and the probe is withdrawn at a speed of 1 mm/sec.

The hardness of the composition is calculated via the following equation:

$$\text{hardness} = \frac{F_{max}}{\text{area of the cylinder}}$$

Hydrophobic Silica Aerogel Particles

Silica aerogels are porous materials obtained by replacing (by drying) the liquid component of a silica gel with air.

They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles used in the present invention have a specific surface area per unit of mass ($S_M$) ranging from 500 to 1500 $m_2/g$, preferably from 600 to 1200 $m_2/g$ and better still from 600 to 800 $m_2/g$, and a size expressed as the mean volume diameter (D[0.5]), ranging from 1 to 30 μm, preferably from 5 to 25 μm, better still from 5 to 20 μm and even better still from 5 to 15 μm.

The specific surface area per unit of mass may be determined via the BET (Brunauer-Emmett-Teller) nitrogen absorption method described in the *Journal of the American Chemical Society*, vol. 60, page 309, February 1938 and corresponding to the international standard ISO 5794/1 (appendix D). The BET specific surface area corresponds to the total specific surface area of the particles under consideration.

The size of the silica aerogel particles may be measured by static light scattering using a commercial granulometer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., "Light Scattering by Small Particles," Chapters 9 and 10, Wiley, New York, 1957.

According to one advantageous embodiment, the hydrophobic silica aerogel particles used in the present invention have a specific surface area per unit of mass ($S_M$) ranging from 600 to 800 $m^2/g$ and a size expressed as the mean volume diameter (D[0.5]) ranging from 5 to 20 μm and better still from 5 to 15 μm.

The silica aerogel particles used in the present invention may advantageously have a tamped density ρ) ranging from 0.04 $g/cm^3$ to 0.10 $g/cm^3$ and preferably from 0.05 $g/cm^3$ to 0.08 $g/cm^3$.

In the context of the present invention, this density, known as the tamped density, may be assessed according to the following protocol:

40 g of powder are poured into a measuring cylinder; the measuring cylinder is then placed on a Stav 2003 machine from Stampf Volumeter; the measuring cylinder is then subjected to a series of 2500 packing motions (this operation is repeated until the difference in volume between two consecutive tests is less than 2%); the final volume Vf of packed powder is then measured directly on the measuring cylinder. The tamped density is determined by the ratio m/Vf, in this instance 40/Vf (Vf being expressed in $cm^3$ and m in g).

According to one embodiment, the hydrophobic silica aerogel particles used in the present invention have a specific surface area per unit of volume $S_V$ ranging from 5 to 60 $m^2/cm^3$, preferably from 10 to 50 $m^2/cm^3$ and better still from 15 to 40 $m^2/cm^3$.

The specific surface area per unit of volume is given by the relationship: $S_V = S_M \cdot \rho$ where ρ is the tamped density expressed in $g/cm^3$ and $S_M$ is the specific surface area per unit of mass expressed in $m^2/g$, as defined above.

Preferably, the hydrophobic silica aerogel particles according to the invention have an oil-absorbing capacity, measured at the wet point, ranging from 5 to 18 ml/g, preferably from 6 to 15 ml/g and better still from 8 to 12 ml/g.

The oil-absorbing capacity measured at the wet point, noted Wp, corresponds to the amount of water that needs to be added to 100 g of particle in order to obtain a homogeneous paste.

It is measured according to the wet point method or the method for determining the oil uptake of a powder described in standard NF T 30-022. It corresponds to the amount of oil adsorbed onto the available surface of the powder and/or absorbed by the powder by measuring the wet point, described below:

An amount=2 g of powder is placed on a glass plate, and the oil (isononyl isononanoate) is then added dropwise. After addition of 4 to 5 drops of oil to the powder, mixing is performed using a spatula, and addition of oil is continued until a conglomerate of oil and powder has formed. At this point, the oil is added one drop at a time and the mixture is then triturated with the spatula. The addition of oil is stopped when a firm, smooth paste is obtained. This paste must be able to be spread on the glass plate without cracking or forming lumps. The volume Vs (expressed in ml) of oil used is then noted. The oil uptake corresponds to the ratio Vs/m.

The aerogels used according to the present invention are hydrophobic silica aerogels, preferably of silylated silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogels particles that have been surface-modified by silylation, reference may be made to document U.S. Pat. No. 7,470,725. Use will be made in particular of hydrophobic silica aerogels particles surface-modified with trimethylsilyl groups (trimethylsilyl silica).

As hydrophobic silica aerogels that may be used in the invention, examples that may be mentioned include the aerogel sold under the name VM-2260 (INCI name: Silica silylate), by the company Dow Corning, the particles of which have a mean size of about 1000 microns and a specific surface area per unit of mass ranging from 600 to 800 m$^2$/g.

Mention may also be made of the aerogels sold by the company Cabot under the references Aerogel TLD 201, Aerogel OGD 201 and Aerogel TLD 203, Enova Aerogel MT 1100 and Enova Aerogel MT 1200.

Use will be made more particularly of the aerogel sold under the name VM-2270 (INCI name: Silica silylate), by the company Dow Corning, the particles of which have a mean size ranging from 5-15 microns and a specific surface area per unit of mass ranging from 600 to 800 m$^2$/g.

The silica aerogel particles in accordance with the invention are preferably present in the cosmetic composition in an amount of active material ranging from 0.5% to 15% by weight and more preferentially from 1% to 10% by weight relative to the total weight of the composition.

Oily Phase

The compositions according to the invention contain at least one water-immiscible organic liquid phase, known as an oily phase. This phase generally comprises one or more hydrophobic compounds that make the said phase water immiscible. The said phase is liquid (in the absence of structuring agent) at room temperature (20-25° C.). Preferentially, the water-immiscible organic-liquid organic phase in accordance with the invention is generally formed from at least one volatile oil and/or non-volatile non-silicone oil and/or a non-volatile silicone oil.

The term "oil" means a fatty substance that is liquid at room temperature (25° C.) and atmospheric pressure (760 mmHg, i.e. 105 Pa). The oil may be volatile or non-volatile.

For the purposes of the invention, the term "volatile oil" means an oil that is capable of evaporating on contact with the skin or the keratin fibre in less than one hour, at room temperature and atmospheric pressure. The volatile oils of the invention are volatile cosmetic oils, which are liquid at room temperature, having a non-zero vapour pressure, at room temperature and atmospheric pressure, ranging in particular from 0.13 Pa to 40000 Pa ($10^{-3}$ to 300 mmHg), in particular ranging from 1.3 Pa to 13000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure of less than $10^{-3}$ mmHg (0.13 Pa).

The oils in accordance with the invention are preferably chosen from any cosmetically acceptable oil, especially mineral, animal, plant or synthetic oils, especially hydrocarbon-based oils, fluoro oils or silicone oils, or mixtures thereof.

The term "hydrocarbon-based oil" means an oil mainly containing carbon and hydrogen atoms and possibly one or more functions chosen from hydroxyl, ester, ether and carboxylic functions. Generally, the oil has a viscosity of from 0.5 to 100 000 mPa·s, preferably from 50 to 50000 mPa·s and more preferably from 100 to 300 000 mPa·s.

The term "silicone oil" means an oil comprising in its structure carbon atoms and at least one silicon atom.

The term "fluoro oil" means partially hydrocarbon-based and/or silicone-based oils comprising carbon atoms and fluorine atoms.

As examples of volatile hydrocarbon-based oils that may be used in the invention, mention may be made of:
volatile hydrocarbon-based oils chosen from hydrocarbon-based oils containing from 8 to 16 carbon atoms, and especially $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_8$-$C_{16}$ esters and isohexyl neopentanoate, and mixtures thereof. Other volatile hydrocarbon-based oils, for instance petroleum distillates, especially those sold under the name Shell Solt by the company Shell, may also be used; volatile linear alkanes, such as those described in patent application DE10 2008 012 457 from the company Cognis.

As examples of non-volatile hydrocarbon-based oils that may be used in the invention, mention may be made of:
hydrocarbon-based oils of animal origin, such as perhydrosqualene;
hydrocarbon-based plant oils such as liquid triglycerides of fatty acids of 4 to 24 carbon atoms, for instance heptanoic or octanoic acid triglycerides, or wheatgerm oil, olive oil, sweet almond oil, palm oil, rapeseed oil, cottonseed oil, alfalfa oil, poppy oil, pumpkin oil, marrow oil, blackcurrant oil, evening primrose oil, millet oil, barley oil, quinoa oil, rye oil, safflower oil, candlenut oil, passion flower oil, musk rose oil, sunflower oil, corn oil, soybean oil, grapeseed oil, sesame seed oil, hazelnut oil, apricot oil, macadamia oil, castor oil, avocado oil, caprylic/capric acid triglycerides, for instance those sold by the company Stéarineries Dubois or those sold under the names Miglyol 810, 812 and 818 by the company Dynamit Nobel, jojoba oil and shea butter oil,
linear or branched hydrocarbons, of mineral or synthetic origin, such as liquid paraffins and derivatives thereof, petroleum jelly, polydecenes, polybutenes, hydrogenated polyisobutene such as Parleam, and squalane,
synthetic ethers containing from 10 to 40 carbon atoms;
synthetic esters, especially of fatty acids, for instance the oils of formula $R_1COOR_2$ in which $R_1$ represents a linear or branched higher fatty acid residue containing from 1 to 40 carbon atoms and $R_2$ represents a hydrocarbon-based chain, which is especially branched, containing from 1 to 40 carbon atoms, with $R_1+R_2 \geq 10$, for instance purcellin oil (cetostearyl octanoate), isononyl isononanoate, isopropyl myristate, isopropyl palmitate, $C_{12}$-$C_{15}$ alkyl benzoates, hexyl laurate, diisopropyl adipate, isononyl isononanoate, 2-ethylhexyl palmitate, 2-octyldodecyl stearate, 2-octyldodecyl erucate, isostearyl isostearate or tridecyl trimellitate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetraisostearate, fatty alcohols that are liquid at room temperature, containing a branched and/or unsaturated carbon-based chain containing from 12 to 26 carbon atoms, for instance octyldodecanol, isostearyl alcohol, 2-butyloctanol, 2-hexyldecanol, 2-undecylpentadecanol or oleyl alcohol, higher fatty acids such as oleic acid, linoleic acid or linolenic acid;

carbonates;

acetates;

citrates.

As examples of partially hydrocarbon-based and/or silicone-based fluoro oils, mention may be made of fluorosilicone oils, fluoro polyethers and fluorosilicones as described in document EP-A-847 752;

As examples of non-volatile silicone oils, mention may be made of linear or cyclic non-volatile polydimethylsiloxanes (PDMS); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates, and mixtures thereof.

According to one particularly preferred form of the invention, the compositions contain less than 2% volatile silicone oil, or even less than 0.5% volatile silicone oil, and are especially free of volatile silicone oil; the volatile silicone oil not being added during the preparation of the composition, but corresponding to the residual volatile silicone oil introduced by the mixed ingredients.

Solid Fatty Substances

The composition according to the invention comprises at least one solid fatty substance preferably chosen from waxes and pasty fatty substances, and mixtures thereof, and more particularly waxes.

Pasty Fatty Substances

For the purposes of the present invention, the term "pasty fatty substance" (also known as a paste) means a lipophilic fatty compound with a reversible solid/liquid change of state, displaying anisotropic crystal organization in the solid state, and comprising a liquid fraction and a solid fraction at a temperature of 23° C.

In other words, the starting melting point of the pasty compound can be less than 23° C. The liquid fraction of the pasty compound measured at 23° C. can represent 9% to 97% by weight of the compound. This liquid fraction at 23° C. preferably represents between 15% and 85% and more preferably between 40% and 85% by weight.

For the purposes of the invention, the melting point corresponds to the temperature of the most endothermic peak observed on thermal analysis (DSC) as described in standard ISO 11357-3; 1999. The melting point of a pasty substance or of a wax may be measured using a differential scanning calorimeter (DSC), for example the calorimeter sold under the name MDSC 2920 by the company TA Instruments.

The measuring protocol is as follows:

A sample of 5 mg of paste or wax (depending on the case) placed in a crucible is subjected to a first temperature rise passing from −20° C. to 100° C., at the heating rate of 10° C./minute, then is cooled from 100° C. to −20° C. at a cooling rate of 10° C./minute and finally subjected to a second temperature rise passing from −20° C. to 100° C. at a heating rate of 5° C./minute. During the second temperature rise, the variation in the difference between the power absorbed by the empty crucible and the crucible containing the sample of paste or wax as a function of the temperature is measured. The melting point of the compound is the temperature value corresponding to the top of the peak of the curve representing the variation in the difference in power absorbed as a function of the temperature.

The liquid fraction by weight of the pasty compound at 23° C. is equal to the ratio of the heat of fusion consumed at 23° C. to the heat of fusion of the pasty compound.

The heat of fusion of the pasty compound is the heat consumed by the compound in order to pass from the solid state to the liquid state. The pasty compound is said to be in the solid state when all of its mass is in crystalline solid form. The pasty compound is said to be in the liquid state when all of its mass is in liquid form.

The heat of fusion of the pasty compound is equal to the area under the curve of the thermogram obtained using a differential scanning calorimeter (DSC), such as the calorimeter sold under the name MDSC 2920 by the company TA Instrument, with a temperature rise of 5° C. or 10° C. per minute, according to standard ISO 11357-3:1999. The heat of fusion of the pasty compound is the amount of energy required to make the compound change from the solid state to the liquid state. It is expressed in J/g.

The heat of fusion consumed at 23° C. is the amount of energy absorbed by the sample to change from the solid state to the state that it has at 23° C., constituted of a liquid fraction and a solid fraction.

The liquid fraction of the pasty compound measured at 32° C. preferably represents from 30% to 100% by weight of the compound, preferably from 50% to 100%, more preferably from 60% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The heat of fusion consumed at 32° C. is calculated in the same way as the heat of fusion consumed at 23° C.

The pasty compound is preferably chosen from synthetic compounds and compounds of plant origin. A pasty compound may be obtained by the synthesis from starting materials of plant origin.

The pasty compound is advantageously chosen from:

lanolin and derivatives thereof, polyol ethers chosen from ethers of pentaerythritol and of polyalkylene glycol, ethers of fatty alcohol and of sugar, and mixtures thereof, the ethers of pentaerythritol and of polyethylene glycol comprising 5 oxyethylene units (5 OE) (CTFA name: PEG-5 Pentaerythrityl Ether), polypropylene glycol pentaerythrityl ether comprising five oxypropylene (5 OP) units (CTFA name: PPG-5 Pentaerythrityl Ether) and mixtures thereof, and more especially the mixture PEG-5 Pentaerythrityl Ether, PPG-5 Pentaerythrityl Ether and soybean oil, sold under the name Lanolide by the company, Vevy, which is a mixture in which the constituents are in a 46/46/8 weight ratio: 46% PEG-5 Pentaerythrityl Ether, 46% PPG-5 Pentaerythrityl Ether and 8% soybean oil;

polymeric or non-polymeric silicone compounds, polymeric or non-polymeric fluoro compounds, vinyl polymers, especially:

olefin homopolymers and copolymers, hydrogenated diene homopolymers and copolymers, linear or branched oligomers, homopolymers or copolymers of alkyl(meth)acrylates preferably containing a $C_8$-$C_{30}$ alkyl group, oligomers, homopolymers and copolymers of vinyl esters containing $C_8$-$C_{30}$ alkyl groups, oligomers, homopolymers and copolymers of vinyl ethers containing $C_8$-$C_{30}$ alkyl groups, liposoluble polyethers resulting from the polyetherification between one or more $C_2$-$C_{100}$ and preferably $C_2$-$C_{50}$ diols, esters, and/or mixtures thereof.

The pasty compound is preferably a polymer, especially a hydrocarbon-based polymer.

Among the liposoluble polyethers that are particularly preferred are copolymers of ethylene oxide and/or of propylene oxide with $C_6$-$C_{30}$ long-chain alkylene oxides, more preferably such that the weight ratio of the ethylene oxide and/or of the propylene oxide to the alkylene oxides in the copolymer is from 5:95 to 70:30. In this family, mention will be made especially of copolymers such that the long-chain alkylene oxides are arranged in blocks having an average molecular weight from 1000 to 10000, for example a polyoxyethylene/polydodecyl glycol block copolymer such as the ethers of dodecanediol (22 mol) and of polyethylene glycol (45 OE) sold under the brand name Elfacos ST9 by Akzo Nobel.

Among the esters, the following are especially preferred:

esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as those sold under the brand name Softisan 649 by the company Sasol, the arachidyl propionate sold under the brand name Waxenol 801 by Alzo, phytosterol esters, fatty acid triglycerides and derivatives thereof, pentaerythritol esters, non-crosslinked polyesters resulting from polycondensation between a linear or branched $C_4$-$C_{50}$ dicarboxylic acid or polycarboxylic acid and a $C_2$-$C_{50}$ diol or polyol, aliphatic esters of an ester, resulting from the esterification of an aliphatic hydroxycarboxylic acid ester with an aliphatic carboxylic acid. Preferably, the aliphatic carboxylic acid comprises from 4 to 30 and preferably from 8 to 30 carbon atoms. It is preferably chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof. The aliphatic carboxylic acid is preferably branched. The aliphatic hydroxycarboxylic acid ester is advantageously derived from a hydroxylated aliphatic carboxylic acid containing from 2 to 40 carbon atoms, preferably from 10 to 34 carbon atoms and better still from 12 to 28 carbon atoms, and from 1 to 20 hydroxyl groups, preferably from 1 to 10 hydroxyl groups and better still from 1 to 6 hydroxyl groups.

The aliphatic hydroxycarboxylic acid ester is chosen from:

a) partial or total esters of saturated linear mono-hydroxylated aliphatic monocarboxylic acids;

b) partial or total esters of unsaturated monohydroxylated aliphatic monocarboxylic acids;

c) partial or total esters of saturated monohydroxylated aliphatic polycarboxylic acids;

d) partial or total esters of saturated polyhydroxylated aliphatic polycarboxylic acids;

e) partial or total esters of $C_2$ to $C_{16}$ aliphatic polyols that have reacted with a monohydroxylated or polyhydroxylated aliphatic monocarboxylic or polycarboxylic acid, and mixtures thereof, esters of a diol dimer and of a diacid dimer, where appropriate esterified on their free alcohol or acid function(s) with acid or alcohol radicals, especially dimer dilinoleate esters; such esters may be chosen especially from the esters having the following INCI nomenclature: bis-behenyl/isostearyl/phytosteryl dimer dilinoleyl dimer dilinoleate (Plandool G), phytosteryl/isostearyl/stearyl/behenyl dimer dilinoleate (Plandool H or Plandool S), and mixtures thereof, hydrogenated rosinate esters, such as dilinoleyl dimers of hydrogenated rosinate (Lusplan DD-DHR or DD-DHR from Nippon Fine Chemical);

and mixtures thereof,

Wax(es)

According to one preferred embodiment, the composition according to the invention comprises at least one wax.

The wax under consideration in the context of the present invention is generally a lipophilic compound that is solid at room temperature (25° C.), with a solid/liquid reversible change of state, having a melting point of greater than or equal to 30° C., which may be up to 200° C. and in particular up to 120° C.

In particular, the waxes that are suitable for the invention may have a melting point of greater than or equal to 45° C. and in particular greater than or equal to 55° C.

The waxes that may be used in the compositions according to the invention are chosen from waxes that are solid at room temperature of animal, plant, mineral or synthetic origin, and mixtures thereof.

Examples that may be mentioned include the following hydrocarbon-based waxes comprising a fatty alkyl chain generally containing from 10 to 60 carbon atoms and preferably from 20 to 40 carbon atoms, the said chain possibly being saturated or unsaturated, substituted or unsubstituted, and linear, branched or cyclic, preferably saturated and linear:

fatty alcohols;

fatty alcohol esters;

fatty acids;

fatty acid amides;

fatty acid esters including triglycerides;

fatty acid ethers;

ethoxylated fatty alcohols;

ethoxylated fatty acids and the corresponding salts thereof.

Among the fatty alcohols, mention may be made of stearyl alcohol and cetearyl alcohol, or mixtures thereof.

Among the fatty alcohol esters, mention may be made of triisostearyl citrate, ethylene glycol bis(12-hydroxystearate), tristearyl citrate, stearyl octanoate, stearyl heptanoate, trilauryl citrate, and mixtures thereof.

Among the fatty acid esters, mention may be made of ester waxes, monoglycerides, diglycerides and triglycerides.

Ester waxes that may be mentioned include stearyl stearate, stearyl behenate, stearyloctyldodecanol, cetearyl behenate, behenyl behenate, ethylene glycol distearate and ethylene glycol dipalmitate. Use may be made in particular of a $C_{20}$-$C_{40}$ alkyl (hydroxystearyloxy)stearate (the alkyl group containing from 20 to 40 carbon atoms), alone or as a mixture. Such a wax is especially sold under the names Kester Wax K 82 P®, Hydroxypolyester K 82 P® and Kester Wax K 80 P® by the company Koster Keunen.

Among the triglyceride waxes, mention may be made more particularly of Tribehenine, $C_{18}$-$C_{36}$ triglycerides, and mixtures thereof.

As illustrations of waxes that are suitable for the invention, mention may be made especially of hydrocarbon-based waxes, for instance beeswax, lanolin wax, Chinese insect waxes, rice bran wax, carnauba wax, candelilla wax, ouricury wax, esparto grass wax, berry wax, shellac wax, Japan wax and sumach wax; montan wax, orange wax and lemon wax, microcrystalline waxes, paraffins and ozokerite; polyethylene waxes, the waxes obtained by Fischer-Tropsch synthesis and waxy copolymers, and also esters thereof.

Mention may also be made of waxes obtained by catalytic hydrogenation of animal or plant oils containing linear or branched $C_8$-$C_{32}$ fatty chains. Among these waxes that may especially be mentioned are isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate sold under the name Hest 2T-4S® by the company Heterene.

Mention may also be made of silicone waxes ($C_{30-45}$ alkyl dimethicone) and fluoro waxes.

The waxes obtained by hydrogenation of castor oil esterified with cetyl alcohol, sold under the names Phytowax ricin 16L64® and 22L73® by the company Sophim, may also be used. Such waxes are described in patent application FR-A-2 792 190.

As microwaxes that may be used in the compositions according to the invention, mention may be made especially of carnauba microwaxes, such as the product sold under the name MicroCare 350® by the company Micro Powders, synthetic microwaxes, such as the product sold under the name MicroEase 1145® by the company Micro Powders, microwaxes consisting of a mixture of carnauba wax and polyethylene wax, such as the products sold under the names Micro Care 300® and 310® by the company Micro Powders, microwaxes consisting of a mixture of carnauba wax and of synthetic wax, such as the product sold under the name Micro Care 325® by the company Micro Powders, polyethylene microwaxes, such as the products sold under the names Micropoly 200®, 220®, 220L® and 250S® by the company Micro Powders, and polytetrafluoroethylene microwaxes, such as the products sold under the names Microslip 519® and 519 L® by the company Micro Powders.

Use will be made more particularly of triglyceride waxes and more particularly Tribehenine, $C_{18}$-$C_{36}$ triglycerides, and mixtures thereof.

The composition according to the invention may comprise a content of solid fatty substance preferably ranging from 1% to 20% by weight and in particular from 2% to 12% by weight relative to the total weight of the composition.

Galenical Forms

The compositions according to the invention may be in the form of a cream, a balm, a pomade or a gel whose hardness may vary as a function of the desired application, the region of human keratin material to be treated and the desired conditioning.

The compositions according to the invention may be conditioned in a jar; in a device equipped with an open-work wall, especially a grille; in a device equipped with a ball applicator ("roll-on"); in the form of wands (sticks). In this regard, they contain the ingredients generally used in products of this type, which are well known to those skilled in the art.

The present invention also relates to a cosmetic process for treating human perspiration and/or perspiration-related body odour, which consists in applying to the surface of a human keratin material at least one composition as defined previously comprising at least one deodorant active agent and/or one antiperspirant active agent.

The compositions in accordance with the invention may thus be used as deodorants and/or antiperspirants and may contain at least one deodorant active agent and/or one antiperspirant active agent.

Additional Antiperspirant Salts or Complexes

The aluminium and/or zirconium antiperspirant salts or complexes are preferably chosen from aluminium halohydrates; aluminium zirconium halohydrates, complexes of zirconium hydroxychloride and of aluminium hydroxychloride with or without an amino acid, such as those described in U.S. Pat. No. 3,792,068.

Among the aluminium salts, mention may be made in particular of aluminium chlorohydrate in activated or unactivated form, aluminium chlorohydrex, the aluminium chlorohydrex-polyethylene glycol complex, the aluminium chlorohydrex-propylene glycol complex, aluminium dichlorohydrate, the aluminium dichlorohydrex-polyethylene glycol complex, the aluminium dichlorohydrex-propylene glycol complex, aluminium sesquichlorohydrate, the aluminium sesquichlorohydrex-polyethylene glycol complex, the aluminium sesquichlorohydrex-propylene glycol complex, aluminium sulfate buffered with sodium aluminium lactate.

Among the aluminium-zirconium salts, mention may be made in particular of aluminium zirconium octachlorohydrate, aluminium zirconium pentachlorohydrate, aluminium zirconium tetrachlorohydrate and aluminium zirconium trichlorohydrate.

The complexes of zirconium hydroxychloride and of aluminium hydroxychloride with an amino acid are generally known as ZAG (when the amino acid is glycine). Among these products, mention may be made of the aluminium zirconium octachlorohydrex glycine complexes, the aluminium zirconium pentachlorohydrex glycine complexes, the aluminium zirconium tetrachlorohydrex glycine complexes and the aluminium zirconium trichlorohydrex glycine complexes.

The aluminium and/or zirconium antiperspirant salts or complexes may be present in the composition according to the invention in a proportion of at least 0.5% by weight and preferably from 0.5% to 25% by weight relative to the total weight of the composition.

Deodorant Active Agents

The compositions according to the invention may also contain one or more additional deodorant active agents.

The term "deodorant active agent" refers to any substance that is capable of masking, absorbing, improving and/or reducing the unpleasant odour resulting from the decomposition of human sweat by bacteria.

The deodorant active agents may be bacteriostatic agents or bactericides that act on underarm odour microorganisms, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts, DPTA (1,3-diaminopropanetetraacetic acid), 1,2-decanediol (Symclariol from the company Symrise), glycerol derivatives, for instance caprylic/capric glycerides (Capmul MCM from Abitec), glyceryl caprylate or caprate (Dermosoft GMCY and Dermosoft GMC, respectively from Straetmans), Polyglyceryl-2 caprate (Dermosoft DGMC from Straetmans), and biguanide derivatives, for instance polyhexamethylene biguanide salts—chlorhexidine and salts thereof; 4-phenyl-4,4-dimethyl-2-butanol (Symdeo MPP from Symrise).

Among the deodorant active agents in accordance with the invention, mention may also be made of—zinc salts, for instance zinc salicylate, zinc gluconate, zinc pidolate; zinc sulfate, zinc chloride, zinc lactate, zinc phenolsulfonate; zinc ricinoleate;

sodium bicarbonate;

salicylic acid and derivatives thereof such as 5-n-octanoylsalicylic acid;

zeolites, especially silver-free metallic zeolites;

alum.

The deodorant active agents may be present in the compositions according to the invention in weight proportions of about 0.01% to 10% by weight relative to the total weight of the composition.

Additives

The compositions according to the invention may also comprise additional cosmetic or dermatological active agents.

The cosmetic compositions according to the invention may also comprise cosmetic adjuvants chosen from opacifiers, stabilizers, preserving agents, polymers, fragrances, thickeners, dermatological or cosmetic active agents, dyestuffs or any other ingredient usually used in cosmetics for this type of application.

Needless to say, a person skilled in the art will take care to select this or these optional additional compounds such that the advantageous properties intrinsically associated with the cosmetic composition in accordance with the invention are not, or are not substantially, adversely affected by the envisaged addition(s).

The dermatological or cosmetic active agents may be chosen especially from moisturizers, desquamating agents, agents for improving the barrier function, depigmenting agents, antioxidants, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, tensioning agents, lipo-restructuring agents, slimming agents, agents for promoting the cutaneous capillary circulation, calmatives and/or anti-irritants, sebo-regulators or anti-seborrhoeic agents, astringents, cicatrizing agents, anti-inflammatory agents and antiacne agents.

The examples that follow serve to illustrate the present invention. The amounts are given as mass percentages relative to the total weight of the composition.

EXAMPLES

| Ingredient | Ex 1 | Ex 2 | Ex A (*) | Ex B (*) | Ex C (*) | Ex D (*) |
|---|---|---|---|---|---|---|
| Wax (1) | 7.5% | 10% | 7.5% | 7.5% | 10% | 0 |
| Antiperspirant (3) | 20% | 20% | 20% | 20% | 20% | 20% |
| Aerogel VM-2270 | 2% | 2% | — | — | — | 2% |
| Oil (2) | qs 100 | qs 100 | qs 100 | qs 100 | qs 100 | qs 100 |
| Aerosil R972 | — | — | 2% | — | — | — |
| Hardness (kPa) | 26 | 65 | 13 | 4.18 | 13.6 | 0.7 |
| Appearance | Fondant solid | Fondant solid | Soft paste | Liquid | Soft paste | Liquid |
| Feel | Soft and dry | Soft and dry | Greasy | Greasy | Greasy | Very greasy |

(*) outside the invention
(1) Tribehenine/$C_{18}$-$3_6$ Triglyceride mixture (6%/1.5% by weight)
(2) Dimethicone 10 cSt/Polydecene/Dimethicone and Dimethicone Crosspolymer (DC 9041 from Dow Corning)/PPG-14 butyl ether mixture (39.7%/26.3%/2%/2% by weight)
(3) Aluminium/zirconium glycine tetrahydroxychloride complex The examples show that the hardness of the product obtained by combining hydrophobic silica aerogel particles and wax is much higher than that of the products obtained using each of the thickeners separately. A texturing effect is observed by using a standard fumed silica (Aerosil R972), but the effect observed is of smaller amplitude and the cosmetic qualities of the product are judged as being inferior (greasy).

Examples of Antiperspirant Compositions

| Ingredients | Ex. 3 | Ex. 4 | Ex. 5 | Ex. 6 | Ex. 7 |
|---|---|---|---|---|---|
| Tribehenine | 6% | 4% | 6% | 6% | 4% |
| $C_{18-36}$ triglyceride | 1.5% | 2.5% | 1.5% | 1.5% | 1% |
| Dimethicone 10 cSt | 39.7% | 39.7% | 39.7% | 39.7% | 39.7% |
| Polydecene | 26.3% | 26.3% | 26.3% | 26.3% | 26.3% |
| Aerogel VM-2270 | 2% | 2% | 2% | 4% | 3% |
| Dimethicone and dimethicone crosspolymer (DC 9041 from Dow Corning) | 2% | 2% | 0 | 2% | 2% |
| PPG-14 butyl ether | 2% | 2% | 2% | 2% | 2% |
| Aluminium/zirconium tetrahydroxychloride | 20% | 20% | 20% | 20% | 20% |

-continued

| Ingredients | Ex. 8 | Ex. 9 | Ex. 10 | Ex. 11 |
|---|---|---|---|---|
| Tribehenine/<br>$C_{18}$-$C_{36}$ triglyceride mixture<br>7.5%/2.5% by weight | — | 10% | 10% | 10% |
| Microcrystalline wax | 10% | — | — | — |
| Polydecene/Dimethicone 50/50%<br>by weight | qs 100 | — | — | — |
| Polydecene/<br>diethylhexyl carbonate<br>50%/50% by weight | — | qs 100 | — | — |
| Dimethicone/diethylhexyl<br>carbonate 50/50% by weight | — | — | qs 100 | — |
| Polydecene/<br>isohexadecane 50/50 | — | — | — | qs 100 |
| Aerogel VM-2270 | 2% | 2% | 2% | 2% |
| PPG-14 butyl ether | 2% | 2% | 2% | 2% |
| Aluminium/zirconium<br>tetrahydroxychloride complex | 20% | 20% | 20% | 20% |

The invention claimed is:

1. An anhydrous composition comprising, in a cosmetically acceptable medium:
   a) at least hydrophobic silica aerogel particles with a specific surface area per unit of mass (SM) ranging from 500 to 1500 m²/g and a size expressed as the mean volume diameter ($D_{[0.5]}$) ranging from 1 to 30 μm;
   b) at least one solid fatty substance selected from the group consisting of waxes and pasty fatty substances, and mixtures thereof;
   c) at least one oil; the said composition having a hardness measured at 32° C. and at a humidity of 40% ranging from 15 kPa to 150 kPa;
   and wherein the anhydrous composition contains less than 0.5% by weight of residual water provided by the mixed ingredients of said composition.

2. The composition according to claim 1, wherein the hydrophobic silica aerogel particles have a specific surface area per unit of mass ranging from 600 to 1200 m²/g.

3. The composition according to claim 1, wherein the hydrophobic silica aerogel particles have a size, expressed as the mean volume diameter, ranging from 5 to 25 μm.

4. The composition according to claim 1, wherein the hydrophobic silica aerogel particles have a specific surface area per unit of mass ($S_M$) ranging from 600 to 800 m²/g and a size expressed as the mean volume diameter (D[0.5]) ranging from 5 to 20 μm.

5. The composition according to claim 4, wherein the hydrophobic silica aerogel particles a size expressed as the mean volume diameter (D[0.5]) ranging from 5 to 15 μm.

6. The composition according to claim 1, wherein the hydrophobic silica aerogel particles have a tamped density (ρ) ranging from 0.04 g/cm³ to 0.10 g/cm³.

7. The composition according to claim 1, wherein the hydrophobic silica aerogel particles have a specific surface area per unit of volume $S_V$ ranging from 5 to 60 m²/cm³.

8. The composition according to claim 1, wherein the hydrophobic silica aerogel particles have an oil-absorbing capacity, measured at the wet point, ranging from 5 to 18 ml/g of particles.

9. The composition according to claim 1, wherein the hydrophobic silica aerogel particles are surface-modified trimethylsilyl silica particles.

10. The composition according to claim 1, wherein it contains less than 2% volatile silicone oil.

11. The composition according to claim 1, wherein the solid fatty substance is chosen from triglycerides of waxes, and mixtures thereof.

12. Composition according to claim 1, wherein it contains at least one antiperspirant active agent and/or one deodorant active agent.

13. The composition according to claim 1, wherein the at least hydrophobic silica aerogel particles have a specific surface area per unit of mass ($S_M$) ranging from 600 to 800 m²/g, and the said composition having a hardness measured at 32° C. and at a humidity of 40% ranging from 20 kPa to 100 kPa.

14. The composition according to claim 1, wherein the hydrophobic silica aerogel particles have a size, expressed as the mean volume diameter, ranging from 5 to 20 μm.

15. The composition according to claim 1, wherein the hydrophobic silica aerogel particles have a size, expressed as the mean volume diameter, ranging from 5 to 15 μm.

16. The composition according to claim 1, wherein the hydrophobic silica aerogel particles have a tamped density (ρ) ranging from 0.05 g/cm³ to 0.08 g/cm³.

17. The composition according to claim 1, wherein the hydrophobic silica aerogel particles have a specific surface area per unit of volume $S_V$ ranging from 15 to 40 m²/cm³.

18. A cosmetic process for treating human keratin materials, wherein it consists in applying to the surface of the keratin material at least one composition as defined in claim 1.

19. A cosmetic process for treating body odor, which consists of in applying to the surface of a human keratin material at least one composition as defined in claim 12.

* * * * *